United States Patent
Donsky

(10) Patent No.: US 7,129,717 B2
(45) Date of Patent: Oct. 31, 2006

(54) SYSTEMS AND METHODS FOR MEASURING TEAR FILM OSMOLARITY

(75) Inventor: Eric Donsky, Los Angeles, CA (US)

(73) Assignee: Ocusense, Inc., San Diego, CA (US)

( * ) Notice: Subject to any disclaimer, the term of this patent is extended or adjusted under 35 U.S.C. 154(b) by 155 days.

(21) Appl. No.: 10/718,498

(22) Filed: Nov. 19, 2003

(65) Prior Publication Data
US 2005/0104606 A1   May 19, 2005

(51) Int. Cl.
*G01R 27/22*   (2006.01)
*G01N 27/07*   (2006.01)

(52) U.S. Cl. ...................... 324/692; 324/724
(58) Field of Classification Search ............... 324/692, 324/724, 448
See application file for complete search history.

(56) References Cited

U.S. PATENT DOCUMENTS

| | | | | |
|---|---|---|---|---|
| 4,123,701 A | * | 10/1978 | Josefsen et al. | 324/448 |
| 4,951,683 A | * | 8/1990 | Davis | 600/383 |
| 5,143,080 A | * | 9/1992 | York | 73/64.47 |
| 5,965,631 A | * | 10/1999 | Nicolson et al. | 523/106 |
| 6,120,460 A | * | 9/2000 | Abreu | 600/558 |
| 6,423,001 B1 | * | 7/2002 | Abreu | 600/405 |
| 6,544,193 B1 | * | 4/2003 | Abreu | 600/558 |
| 7,017,394 B1 | * | 3/2006 | Sullivan | 73/64.47 |
| 2002/0196429 A1 | * | 12/2002 | Russell et al. | 356/124 |

OTHER PUBLICATIONS

Ogasawara et al. "Electrical conductivity of tear fluid in healthy persons and keratoconjunctivitis sicca patients measured by a flexible conductimetric sensor", Springer-Verlag 1996, 542-546.*

* cited by examiner

*Primary Examiner*—Hezron Williams
*Assistant Examiner*—Ryan Christensen
(74) *Attorney, Agent, or Firm*—Baker & McKenzie

(57) ABSTRACT

An osmolarity measuring system is configured to receive a contact lens in a measurement chamber. The measurement chamber includes a volume of fluid, and a series of electrodes are configured to measure the electrical properties of the fluid. A processing device correlates the measured electrical properties with an osmolarity measurement. Further, the processing device is configured to track trends in stored osmolarity measurements and alert the user to take an action, including the cessation or alteration of product use.

76 Claims, 5 Drawing Sheets

SYSTEMS AND METHODS FOR MEASURING TEAR FILM OSMOLARITY

RELATED APPLICATION INFORMATION

This application is related to U.S. Utility application Ser. No. 10/400,617 entitled, "Tear Film Osmometry", filed on Mar. 25, 2003 that claims priority under 35 USC ¶119 to U.S. Provisional Patent Application Ser. No. 60/401,432, that was filed on Aug. 6, 2002, both of which was incorporated herein in their entirety as if set forth in full.

BACKGROUND

1. Field of the Inventions

The field of the invention relates generally to osmolarity measurements and more particularly to the use of a contact lens as an ex-vivo receiving substrate to collect tears for subsequent tear film osmolarity measurements.

2. Background Information

Tears fulfill an essential role in maintaining ocular surface integrity, protecting against microbial challenge, and preserving visual acuity. These functions in turn, are critically dependent upon the composition and stability of the tear film structure, which includes an underlying mucin foundation, a middle aqueous component, and an overlying lipid layer. Disruption, deficiency, or absence of the tear film can severely impact the eye.

An increased salt concentration (osmolarity) of the human tear film has been identified as the underlying causative mechanism for all types of dry eye. Chronically heightened osmolarity is tied to post-LASIK complications, keratoconjunctivitis sicca, and contact-lens induced dry eye. While its usefulness as a marker of tear film health is evident, the ability to rapidly measure tear osmolarity has eluded science for decades. If it were possible to measure and, more importantly, monitor the relative tear film osmolarity over time, the quality of health care that could be provided to dry eye patients would increase dramatically. Personalized data about the state of one's disease would allow physicians to develop new therapies, alter prescriptions, and modulate the type of products used in a timely fashion.

For example, the day-to-day response of the tear film is of particular interest when challenged by the deleterious effects of contact lens wear. Irritation caused by contact lenses may lead to an inflammatory condition that exacerbates dry eye symptoms and causes lens wearers considerable discomfort. Often, when getting fitted for a new prescription, a patient must try several different types of lenses before finding a brand that is optimized for their individual ocular surface. The fitting process is largely trial and error because the clinician lacks the ability to track the patient's response over time. Further, because deleterious inflammatory effects may take a few hours to days to occur, it is not feasible to gather this data while the patient is sitting in a clinician's office.

The same constraints hold for monitoring the efficacy of dry eye therapeutics, whether pharmaceutical, tear replacement, or mechanical, i.e. goggles, punctal plugs, etc. Physicians have no means to collect, or correlate patient data, i.e. race, age, gender, medications taken, etc. with signs and symptoms over time. Likewise, scientists would benefit greatly from this data when developing new techniques to treat the disease.

Prevalent technologies require collection of tears by gently touching a glass capillary to the lower lid. However, such technologies are not amenable to "at home" testing. Furthermore, the clinical equipment necessary to analyze the tear film is far too expensive for personal monitoring of tear film health.

SUMMARY OF THE INVENTION

An osmolarity measuring system allows for the ex-vivo measurement of tear film osmolarity. In one aspect, the system is configured to receive a contact lens in a volume of fluid. The contact lens is used to collect a portion of tear film, a submerged series of electrodes are configured to measure the electrical properties of the receiving fluid and a processing device is configured to detect a change in the electrical properties of the receiving fluid in the measurement chamber after the lens has been introduced. The processing device is also configured to correlate the change in electrical properties with an osmolarity measurement.

In another aspect, the osmolarity measuring system includes a memory device to store a plurality of osmolarity measurements. The processing device is configured to track trends in the stored osmolarity measurements and alert the user to take an action, including the cessation or alteration of product use. These and other features, aspects, and embodiments of the invention are described below in the section entitled "Detailed Description of the Preferred Embodiments."

BRIEF DESCRIPTION OF THE DRAWINGS

Features, aspects, and embodiments of the inventions are described in conjunction with the attached drawings, in which.

DETAILED DESCRIPTION OF THE PREFERRED EMBODIMENTS

The systems and methods described below allow a rapid, inexpensive estimate of tear film osmolarity that can be made either at home or in the clinic by using a contact lens as a tear film collection methodology. Generally, a previously worn contact lens can be removed and placed inside a disposable chamber that houses a precisely measured volume of fluid. The disposable element also contains a set of measuring electrodes that can be shielded from direct contact with the lens. A change in the electrical properties of the fluid due to the introduction of the lens can then be correlated to the osmolarity of the patient's tear film. Collected osmolarity readings can, depending on the embodiment, be stored locally on removable memory or uploaded to a central server which can then track and analyze the data.

It should be noted that the systems and methods described herein provide volume dependent methods for determining osmolarity. Specifically, any fluid left on the contact lens surface will alter the final measured concentration of the volume of fluid in the measurement chamber. Often there can be a variation in the day-to-day fluid volume used to make a measurement according to the methods and systems described herein; however, the variability in day to day residual volume is generally irrelevant when measurements corresponding to many timepoints are gathered. The more data that is available, the more that long term trends will be insensitive to random noise caused, for example, by a variation in the fluid volume used to make the osmolarity measurement. Further, residual fluid evaporates quickly from the surface of the lens, which implies that the dynamics of salt dissolution can allow the systems and methods described herein to compensate for changes in volume of the introduced sample. Thus, the systems and methods described herein allow relative changes in osmolarity over time for a single person to be tracked, while enabling information sharing of the data between, for example, a patient and a clinician.

Figure 1A:
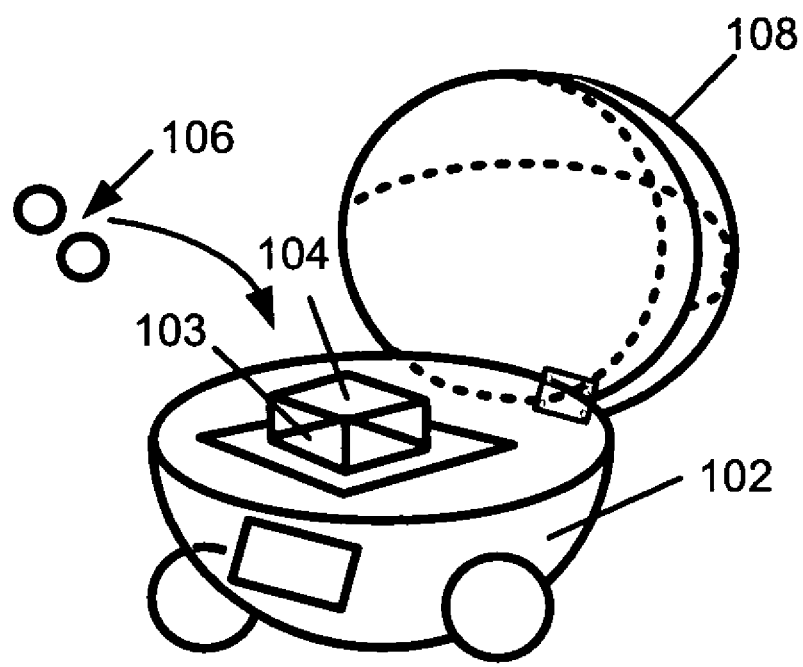
FIGS. 1A, and 1B are diagrams illustrating an osmolarity measuring system with an example embodiment of the invention.
Figure 1B:
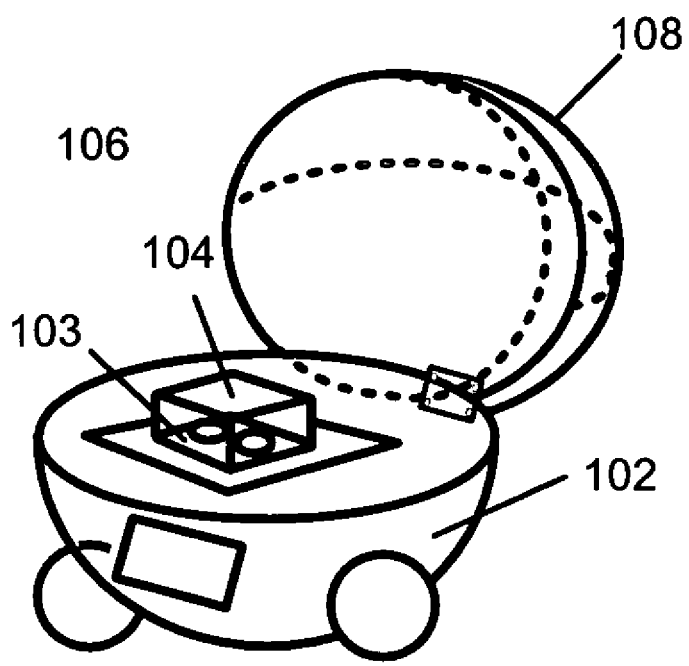

FIG. 1A is a diagram illustrating an example embodiment of an osmolarity testing system 100 configured in accordance with one embodiment of the systems and methods described herein. System 100 comprises a base unit 102 and a cartridge 103. The cartridge 103 includes measurement chamber 104, which is configured to contain a volume of fluid and receive a contact lens 106 in the volume of fluid. In one example of the systems and methods described herein, the contact lens 106 or set of lenses acts as a receiving substrate and can be used to introduce a solute into the measurement chamber 104. In one example embodiment shown in FIG. 1A., the base unit 102 includes a cover 108. In FIG. 1A, the cover 108 is illustrated in the open position, which provides access to measurement chamber 104. The contact lens can be placed into chamber 104 as shown by the arrow in between contact lens 106 and chamber 104. FIG. 1B further illustrates the example osmolarity testing system of FIG. 1A, showing a set of contact lens 106 within chamber 104.

Figure 2:
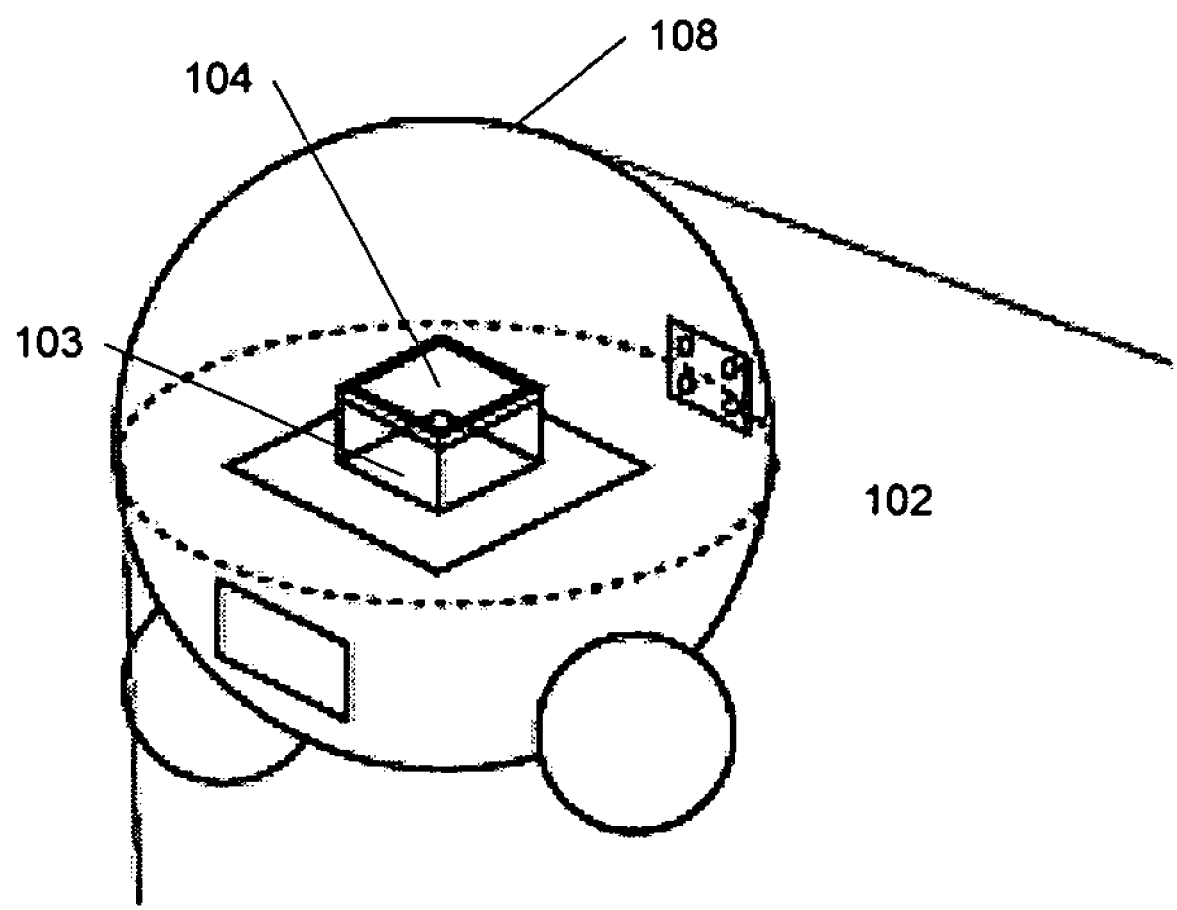
FIG. 2 is a diagram illustrating an osmolarity measuring system with another example embodiment of the invention.

FIG. 2 is a diagram illustrating another example embodiment of an osmolarity testing system 100 configured in accordance with the systems and methods described herein. In FIG. 2, the cover 108 is illustrated in the closed position. In this closed position, the cover 108 provides the additional advantage of minimizing the entry of any unwanted material into the measurement chamber 104 before the osmolarity measurement is taken by the system 100.

The base unit 102 can house the requisite electronics that are required, for example, to provide a voltage, or current, to the measurement chamber 104. The voltage can be provided through batteries located within the base unit 102. Alternatively, the voltage can be provided through an external power source such as a standard wall outlet. As discussed in greater detail below, the base unit 102 can further comprise a processing device, a memory device, a network interface, and/or a signalling device.

Figure 3A:
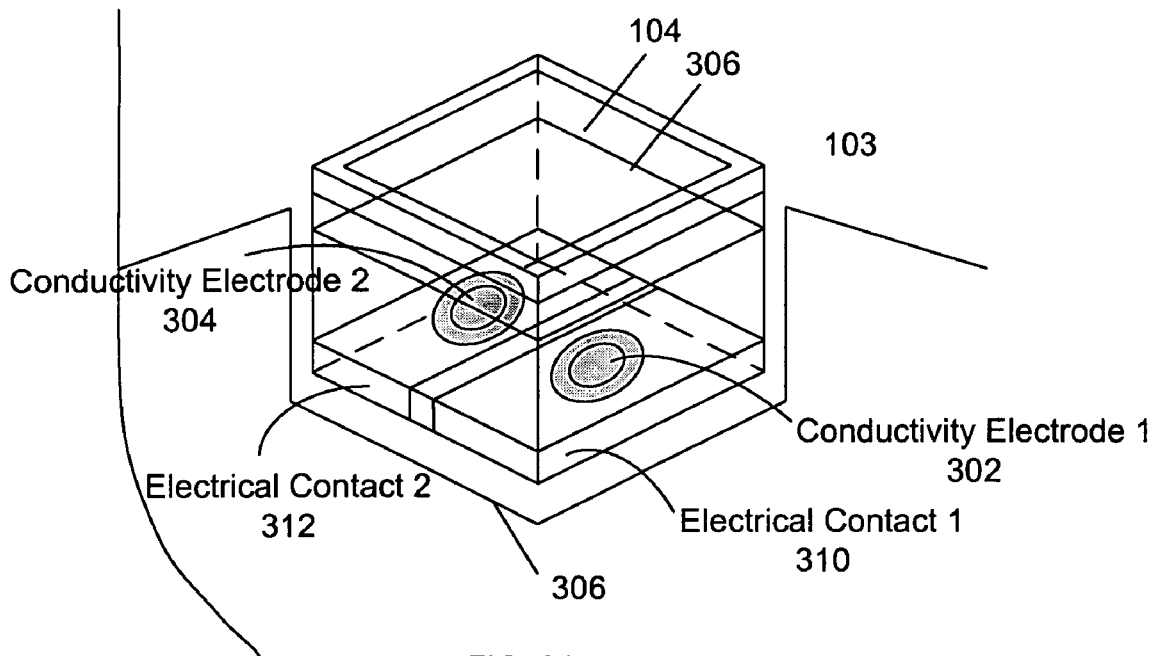
FIGS. 3A, and 3B are diagrams illustrating an osmolarity measuring system of FIGS. 1 A–B in more detail.

FIG. 3A further illustrates one embodiment of the cartridge 103 that includes measurement chamber 104 shown in an enlarged view. The measurement chamber can comprise a plurality of electrodes 302 and 304 printed on the base region 306 of the measurement chamber 104. The measurement chamber 104 can further comprise a plurality of electrical contacts 310 and 312 for communicating with the base unit 102.

Above the electrodes 302 and 304 a barrier 308 can be included that can be configured to facilitate fluidic communication with the electrodes 302 and 304, yet ensure that the contact lens 106 does not directly touch the electrodes 302 and 304. In the absence of the barrier 308, the contact lens can be allowed to physically contact the electrodes 302 and 304 and create a differential resistance path for measuring the current. Depending on the embodiment, the barrier 308 can be comprised of a porous plastic screen, a semi-permeable membrane, or a series of plastic pyramids imprinted on the base region 306 of the measurement chamber 104 to facilitate mass production.

The measurement chamber 104 can be configured to contain a volume of fluid. In one embodiment, the fluid inside the measurement chamber 104 can be deionized water. Deionized water has the benefit of having low conductivity, such that, in one particular embodiment, the introduction of salt ions from the tear film on the contact lens 106 will cause a profound change in the measured electrical properties of the fluid. In another embodiment, a volume of a standardized salt solution of known conductivity can be used. In yet another embodiment, the fluid may be oil based, or comprise a base of some other substance comprising a density lower than that of water. In such embodiments, tear fluid from the contact lens will migrate down the electrode surface at the base of the cartridge and initiate a specific change in local conductivity without dissolving into the bulk fluid.

In another embodiment of the systems and methods described herein, the measurement chamber 104 can be included in a disposable cartridge 103. The cartridge 103 can, in such embodiments, be configured to snap into position in the base unit 102. Further, the measurement chamber 104 can, depending on the implementation, comprise the electrodes 302 and 304, electrical contacts 310 and 312, and the barrier 308. The cartridge 103 can further include a volume of a fluid, such as deionized water, and be sealed with a cover. After the cartridge 103 is snapped into the base unit 102, the sealed cover can be removed from the top of the cartridge to expose the fluid beneath. The cover, whether foil, plastic or a combination of other materials, can also be coated with a hydrophobic material to discourage water from adhesion to the top of the disposable cartridge during shipment.

As discussed above, the systems and methods described herein provide a volume dependent osmolarity measuring system. Therefore, one embodiment that includes a cartridge 103 with a predetermined volume of fluid in the measurement chamber 104 helps to encourage the use of a consistent volume of fluid for the osmolarity measurements over time. In addition, the disposable cartridge can be discarded after each use and a new disposable cartridge can be used to take each osmolarity measurement. Therefore, each osmolarity measurement can begin with a measurement chamber 104 that is substantially free from any interfering solute or particles that could effect the accuracy of the osmolarity measurement.

In another embodiment, the base unit 102 will house the measurement chamber 104. The base unit 102 will further house static electrodes within the measurement chamber 104 and a barrier to prevent the contact lens from contacting the electrodes. In one embodiment, the user will be given a bottle of fluid that has a precision measuring system attached such as a home use pipette, a syringe type dispenser attached to the bottle cap, or another similar system. The user will fill the measurement chamber 104 in the base unit 102 to an indicated volume so that substantially the same volume of fluid is dispensed every time. The user will then place a contact lens 106 in the fluid in the measurement chamber 104. As distinguished from the disposable cartridge described above, the user will be required to empty the fluid from the measurement chamber 104 after each use, and perhaps rinse the measurement chamber 104 to remove any remaining solute or other particles.

In embodiments that use disposable cartridges 103, the base unit 102 can be configured to either auto-sense the introduction of the cartridge 103 via embedded control circuitry or be alerted to the introduction of the cartridge by user input. Insertion of the cartridge 103 into the base unit 102 should result in the requisite electrical connections between electrical contacts 310 and 312 with the base unit 102. The electrical connections should enable the base unit 102 to communicate power and information to and from the cartridge.

In one embodiment, the base unit 102 includes a processing device (not shown) to measure the change in conductivity across the electrodes 302 and 304 at the base 306 of the cartridge 103. In general, the change in conductivity is detected by applying a voltage, or current signal, across the electrodes 302 and 304. A resulting current, voltage, or resistance across the electrodes can then be measured using the processing device. The measurement can then be correlated to an osmolarity value as described below.

For example, in one specific embodiment, a 100 kHz sine wave signal is imparted between the electrodes 302 and 304. An auto-balancing bridge method, for example, can then be used to measure the resulting current through an op-amp stabilized resistor in series with the sample fluid of interest. The conductivity will then be directly related to osmolarity. Thus, in one embodiment, the processing device can access a look-up table, or set of functions, to back-calculate the osmolarity from the measured electrical properties of the sample fluid.

It should be noted, however, that there does exist a fundamental assumption that the volume of fluid added via the contact lens is negligible compared to the volume of fluid inside the cartridge. For example, if the measurement chamber 104 contains a volume of approximately 5 mL, and the contact lens contains 10 µL of residual fluid, which is on the high end of possible collected tear volume, then the volume in the chamber changes by only 0.2%. The salt concentration, and hence conductivity, however, will be significantly altered. For example, the method just described can be sensitive enough to track evaporation of a few nanoliters of fluid on top of an electrode array.

It is likely and expected that volume collections will vary greatly between contact lens type, and between patients over a few weeks of monitoring; however, the same person using the same contact lens will likely collect substantially the same amount of fluid each day. Random noise on top of the day-to-day signal should be insignificant over time because worthwhile trends will be mean squared convergent, and offer the ability to perform linear or nonlinear regression analysis with confidence.

In order to compensate for the volume of the contact lens itself, an input device, such as an infrared bar code reader can be placed on the base unit 102 to collect information about the brand and size of the lens being used. Often, this type of information is only necessary to collect when the user changes contact lens types.

In one embodiment, the base unit 102 can also include a memory device (not shown) to store a plurality of osmolarity measurements. The processed data, as well as any analysis or processing results, can then be stored locally, e.g., in the memory device. Alternatively, this type of information can be uploaded to a server via the network connection and stored remotely as described below. Time and date stamps can also be provided for each measured data point and stored along with the data.

The memory device can be in the form of a removable media such as a flash memory card, memory stick device, USB key, or another similar device. The ability to store data in a removable format can, for example, enable the patient to bring their data to their health care professional during appointments. The clinician can then place the memory card into a computer system, or specially formatted base unit, e.g., with a small LCD screen, capable of displaying the trend in osmolarity. Thus, for example, therapeutic progress can be tracked for a treatment program being administered to the patient. The ability to monitor the therapeutic progress can be used to assist a clinician in their diagnosis or prescription.

In another embodiment, the memory device can housed in the base unit 102 and the base unit 102 can further includes a network connection (not shown). Information stored in the memory device can then be accessed, for example, via the network connection, e.g., the base unit can be connected to the Internet via a dialup, a persistent connection, or a wireless network connection in the user's home. As the memory device of the base unit 102 collects data, it can be uploaded to a central server, which can then perform the osmolarity calculations described above.

Alternatively, the processing device in the base unit 102 can be configure to perform all data processing locally and, e.g., communicate a trend in the data to the server. The trends in the stored osmolarity data can be recognized by linear or nonlinear regression methods, moving average models, autoregressive stochastic models, correlation with predefined statistical models, neural network based classifiers, or pattern recognition formulae, to name a few.

Statistical analysis of the data can also be used to eliminate outlier points in case a test was particularly poorly performed by the patient. For example, if the patient inadvertently introduced a foreign substance into the measurement chamber 104 or onto the contact lens 106 before placing it into the measurement chamber 104, a mechanism for eliminating this erroneous test point is useful. In one embodiment, for example, a predetermined variance from mean based on gaussian, or uniform random variables fitted to typical user data can be applied to users during the first few months of use. Over time, these estimates of variance can be altered to meet each users individual profile. Of course, this is optional, and in other embodiments a static variance model can be used for everyone.

A power source, such as batteries and/or power supply, can also be included in base unit 102. In fact, in one embodiment, waterproof backup batteries can be supplied with the base unit 102 in case it gets unplugged or the power goes out. Alternatively, the base unit would simply ask for the user to input the date and time whenever power was interrupted.

In one embodiment, the processing device can analyze stored osmolarity data and alert the user to a trend in the measured osmolarity. For instance, if after collecting three weeks of data from a patient, a distinctive upward trend in osmolarity is identified by the processing device, it can alert the user and further indicate a specific action that should be taken. Generally, action commands should be simply interpreted to tie in with cessation or alteration of product use.

In one example embodiment, a set of lenses can be provided with the system 100. Once the processing device has detected a precipitous increase in day-to-day osmolarity, a built in indicator could indicate that the user should switch to an alternate pair of contact lenses. The indicator can, for example, comprise a LCD screen, one or more LEDs, a plurality of light indicators, and/or an auditory signal in the form of spoken direction, or other audible signal, to name just a few.

When system 100 is packaged with a set of lenses as described, the set of lenses can be provided in an array of packages that are coded, either by color or other means, to correlate a particular pair of contact lenses to a particular set of physical properties. The set of lenses can therefore provide a broad range of lenses with varying porosity, composition, stiffness, or any other property of the lens that would be optimal to reverse or maintain the current trend in osmolarity. The processing device can then be configured to analyze the osmolarity data and determine which pair of contact lenses from the set will provide the best adjustment for the user given the current trend in osmolarity data. The indicator can then signal the user to switch to a particular set of lenses through the coding system described above. As an example, the LCD screen could light up with a pale red color to indicate that the user should switch to the contact lenses contained in the accompanying pale red colored package.

In another embodiment, a set of artificial tears can be provided with the system 100. The set of artificial tears can be provided in an array of packages that are coded, either by color or other means, to correlate a particular artificial tear solution to a particular set of physical properties. The set of artificial tears can therefore provide a broad range of therapeutic properties based on varying the isotonic, hypotonic, or hypertonic properties of the artificial tears, or any other property of the tears that would be optimal to reverse or maintain the current trend in osmolarity. The processing device can then be configured to analyze the osmolarity data and determines which artificial tear solution from the set will provide the best therapeutic effect for the user given the current trend in osmolarity data. The indicator can then signal the user to switch to a particular artificial tear solution through the coding system described above. As an example, the LCD screen could light up with a pale red color to indicate that the user should switch to the artificial solution contained in the accompanying pale red colored package.

In another embodiment, a set of medications can be provided with the system 100. The set of medications can be provided in an array of packages that are coded, either by color or other means, to correlate a particular medication to a particular set of physical properties. The set of medications can therefore provide a broad range of therapeutic properties. The processing device can be configured to then analyze the osmolarity data and determine which medication from the set will provide the best therapeutic effect for the user given the current trend in osmolarity data. The indicator can then signal the user to switch to a particular medication through the coding system described above. As an example, the LCD screen could light up with a pale red color to indicate that the user should switch to the medication contained in the accompanying pale red colored package.

Figure 3B:
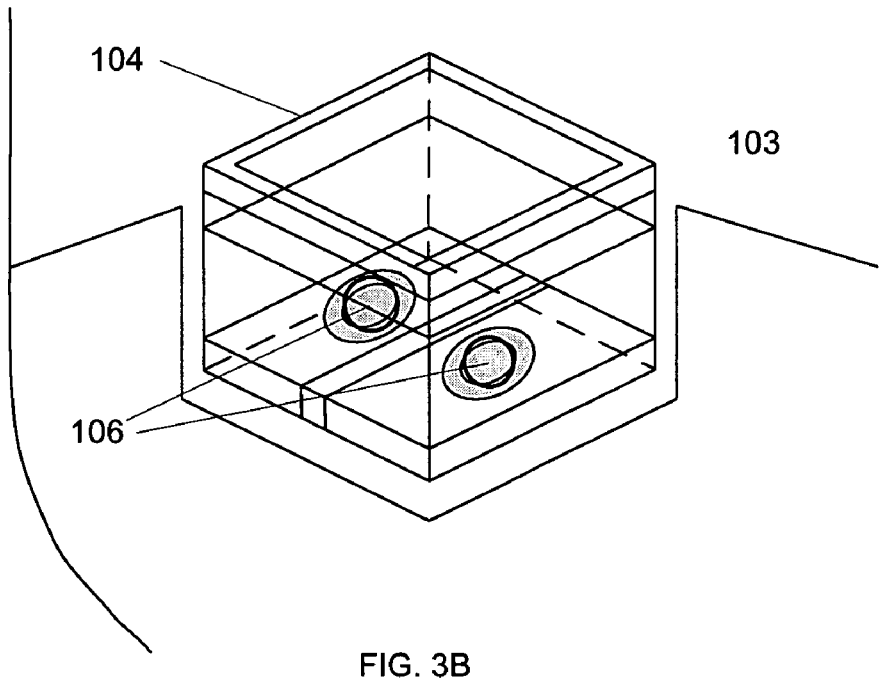

FIG. 3B further illustrates the embodiment of the cartridge 103 and includes a set of contact lens in chamber 104. Cartridge 103 is shown in an enlarged view. As discussed above, chamber 104 is configured to contain a volume of fluid a contact lens 106 or a set of contact lenses.

Figure 4:
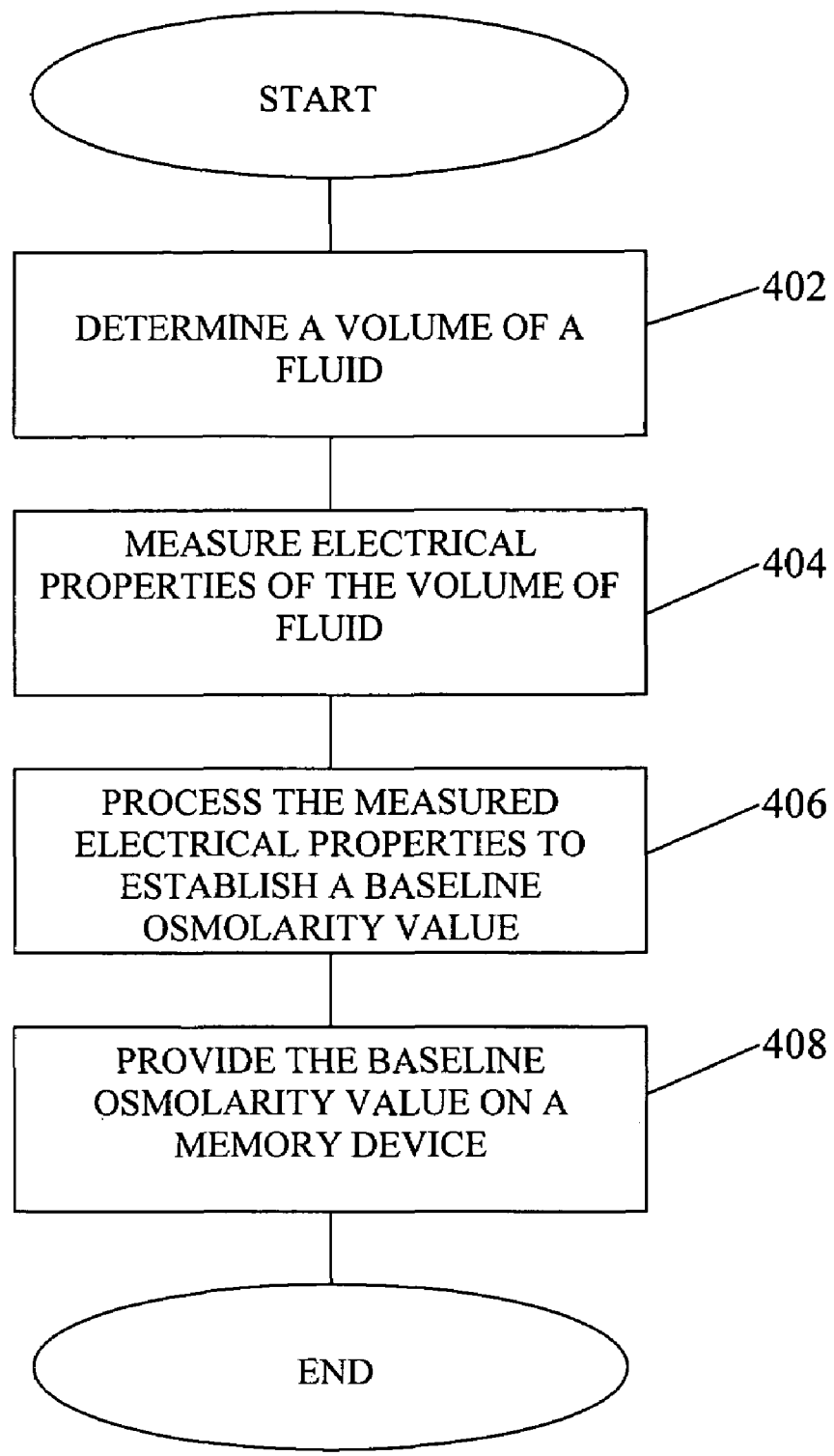
FIG. 4 is a flow chart illustrating a method for configuring an osmolarity measuring system in accordance with an example embodiment of the invention.

FIG. 4 is a flow chart illustrating an example embodiment of a method for configuring an osmolarity testing system in accordance with one embodiment of the systems and methods described herein. First, in step 402, a volume of fluid can be selected to be used when testing osmolarity using the osmolarity testing system. For example, the volume of fluid can be substantially determined based on the dimensions of the measurement chamber, or vice versa. But in any event, the volume selected should be enough to ensure that effective measurements can be made, and to ensure that any fluid introduced via lens 106 is minimal compared to the overall volume.

In one embodiment, the volume selected is approximately 5 mL of fluid. As mentioned above, the fluid itself can be deionized water, which has the benefit of having a low conductivity, so that the introduction of salt ions from the tears will have a profound change in the electrical properties of the fluid. In another embodiment, a volume of a standardized salt solution, an oil based solution, etc., can be used.

The electrical properties associated with the determined fluid volume can then be measured in step 404. In one embodiment, measuring the electrical properties can include measuring the electrical conductivity of the fluid by providing a plurality of electrodes within the measurement chamber and bringing the liquid into contact with the electrodes. A current is then applied to the liquid through the plurality of electrodes. For example, a voltage source can be used to impart a 1 V, 100 kHz sine wave between the electrodes.

The measured electrical properties are then processed to establish a baseline osmolarity value for the system at step 406. In one embodiment of the systems and methods described herein, a processing device is coupled to the measurement chamber to measure the electrical properties, including the electrical conductivity of the fluid as described above. A look-up table, or set of functions, that correlate electrical property values with osmolarity can then be used to back calculate the osmolarity from the measured signals. The calculated osmolarity can then be used to establish a baseline osmolarity value, in step 408 for the selected volume of fluid that can be implemented to test the osmolarity of sample fluids. For example, if the electrical property being measured is conductivity of the fluid, a table that correlates conductivity with osmolarity can then be used to establish the baseline.

The baseline value can then be loaded into base unit 102, e.g., loaded into the memory device included therein, so that it can be used to make osmolarity measurements as described above. In other words, deviations in osmolarity due to residual tear film introduced into measurement chamber 104 via lens 106 can be detected as a deviation from the baseline established as described in the flow chart of FIG. 4.

Figure 5:
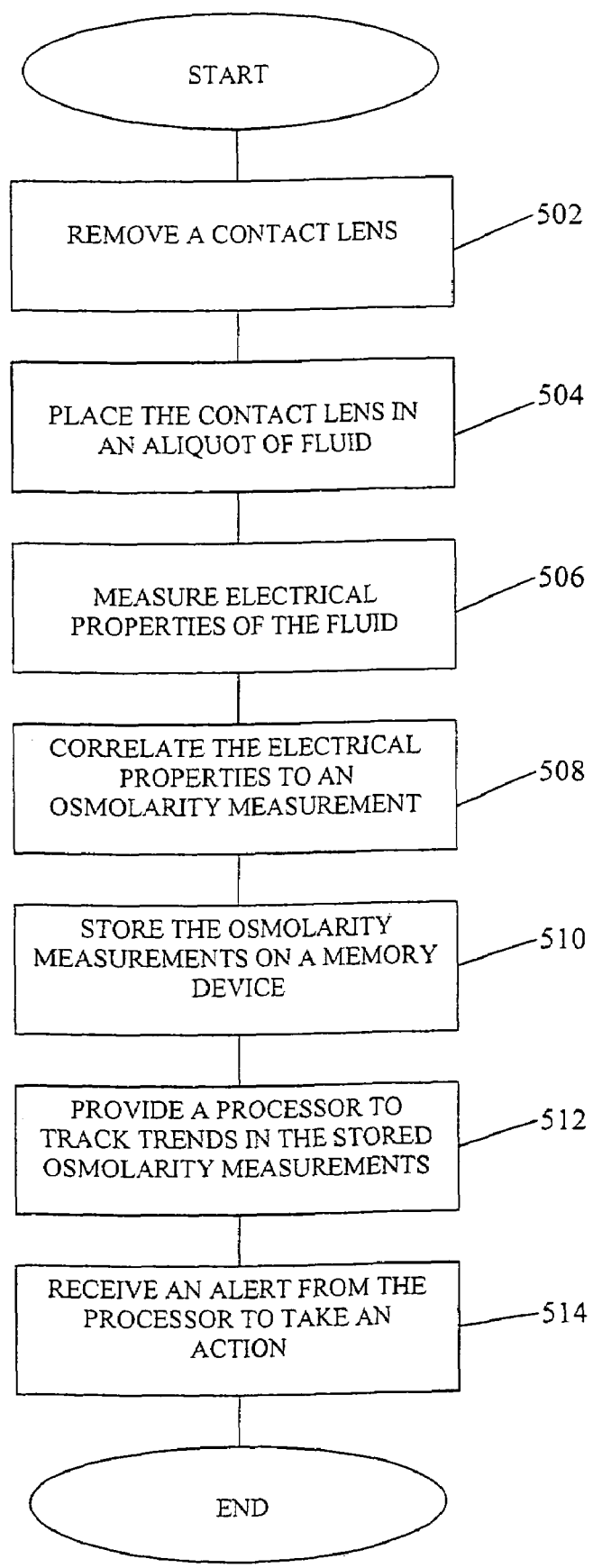
FIG. 5 is a flow chart illustrating a method for using an osmolarity measuring system in accordance with an example embodiment of the invention.

FIG. 5 is a flow chart illustrating an example embodiment of a method for measuring the osmolarity of a sample in accordance with one embodiment of the systems and methods described herein. First, in step 502, the user removes his or her contact lens. In one embodiment, for example, after washing and drying their hands, the user will remove their contact lens and wait for roughly 10 seconds to allow evaporation to desiccate the surface of the lens.

In step 504, the user can then place the removed lens in an aliquot of fluid. In one embodiment, the fluid can be contained in a measurement chamber that is included in a cartridge. In such embodiments, the user will place the cartridge into the base unit and remove the cover from the cartridge before placing the lens in the fluid. In another embodiment, the user will pour a volume of fluid into a measuring chamber that is located in a base unit before placing the lens in the fluid. As previously discussed, the fluid can, for example, be deionized water or a standardized salt solution of known conductivity. Tear fluid from the contact lens can then migrate down the electrode surface at the base of the cartridge and initiate a specific change in local conductivity without dissolving into the bulk fluid.

The electrical properties associated with the fluid are then measured in step 506. In one embodiment, measuring the electrical properties includes measuring the electrical conductivity, resistivity, or complex impedance, etc., of the fluid by providing a plurality of electrodes within the measurement chamber and bringing the liquid into contact with the electrodes. A current is then applied to the liquid through the plurality of electrodes. For example, a voltage source can be used to impart a 1 V peak to peak 100 kHz sine wave between the electrodes.

The measured electrical properties are then processed to establish the osmolarity value for the fluid in step 508. The methods and procedures for processing the measured electrical properties include the methods and procedures that have been previously described.

In step 510, the osmolarity measurement can be stored in a memory device. The memory device can be configured to store a plurality of osmolarity measurements. Therefore, over time, the user will establish a database of measured osmolarity values. The systems and methods described herein can further comprise providing a base unit to include the processing device and the memory device. A table that maps electrical properties to osmolarity values, or alternatively, a set of functions that will back calculate osmolarity values can also be stored in the memory device and used by the processing device to determine osmolarity measurements. Further, as described, the table or set of functions can be configured to account for previously established baseline osmolarity values.

In step 512, e.g., the processing device can be used to identify and track trends in the plurality of osmolarity measurements stored on the memory device. The trends in the stored osmolarity data can be recognized by linear or nonlinear regression methods, moving average models, autoregressive stochastic models, correlation with predefined statistical models, neural network based classifiers, or pattern recognition formulae.

In step 514, the processor can analyze the trends in the osmolarity data and the user can receive an alert based on the trend in the measured osmolarity. For instance, if after collecting three weeks of data from a patient, a distinctive upward trend in osmolarity is identified by the processing device, it can alert the user and further indicate a specific action that should be taken. As previously discussed, the user can receive an alert to change to a new set of lenses, administer a particular type of artificial tears, or take a particular type of medication to help restore the proper osmolarity to the ocular surface.

While certain embodiments of the inventions have been described above, it will be understood that the embodiments described are by way of example only. Accordingly, the inventions should not be limited based on the described embodiments. Rather, the scope of the inventions described herein should only be limited in light of the claims that follow when taken in conjunction with the above description and accompanying drawings.

What is claimed:

1. An osmolarity measuring system, comprising:
   a measurement chamber configured to receive a volume of fluid and to receive a lens, the lens configured to carry a certain amount of tear film;
   a series of electrodes configured to measure the electrical properties of fluid in the measurement chamber;
   a processing device coupled to the series of electrodes, the processing device configured to detect a change in the electrical properties of the fluid in the measurement chamber when a lens is placed in the measurement chamber.

2. The osmolarity measuring system of claim 1, wherein the processing device is configured to correlate the change in electrical properties with an osmolarity measurement.

3. The osmolarity measuring system of claim 1, further comprising a plurality of electrode pairs, the plurality of electrode pairs configured to measure the electrical properties of the fluid.

4. The osmolarity measuring system of claim 1, wherein the pair of electrodes is configured to avoid direct contact with the lens when the lens is placed in the measuring chamber.

5. The osmolarity measuring system of claim 1, wherein measuring the electrical properties comprises measuring the electrical conductivity, or complex impedance of the fluid.

6. The osmolarity measuring system of claim 1, wherein the fluid is deionized water.

7. The osmolarity measuring system of claim 2, further comprising a display coupled with the processor, wherein the processor is further configured to display the osmolarity measurement on the display.

8. The osmolarity measuring system of claim 2, further comprising a memory coupled with the processing device, the memory configured to store a table that maps electrical properties with osmolarity values, and wherein the processor is configured to correlate the change in electrical properties with an osmolarity value using the table.

9. The osmolarity measuring system of claim 8, wherein the table is configured to account for a baseline osmolarity associated with the volume of fluid that the measurement chamber is configured to receive.

10. The osmolarity measuring system of claim 9, wherein the memory is configured to store a plurality of osmolarity measurements.

11. The osmolarity measuring system of claim 10, wherein the memory device is removable.

12. The osmolarity measuring system of claim 10, wherein the processor is further configured to track trends in the plurality of osmolarity measurements.

13. The osmolarity measuring system of claim 12, further comprising an indicator to tell the user to perform an action.

14. The osmolarity measuring system of claim 13, wherein the indicator comprises at least one of a display, an LED, a plurality of lights, or an auditory signal.

15. The osmolarity measuring system of claim 13, wherein the indicator is configured to indicate a type of artificial tears to administer.

16. The osmolarity measuring system of claim 13, wherein the indicator is configured to indicate a type of medication to administer.

17. The osmolarity measuring system of claim 13, wherein the indicator is configured to indicate a type of contact lens to use.

18. The osmolarity measuring system of claim 10, further comprising a base unit to include the processing device.

19. The osmolarity measuring system of claim 18, wherein the base unit is configured to include the measurement chamber.

20. The osmolarity measuring system of claim 18, wherein the base unit is configured to receive a cartridge that includes the measurement chamber.

21. The osmolarity measuring system of claim 20, wherein the measurement chamber is configured to be disposable.

22. The osmolarity measuring system of claim 21, further comprising a pair of electrodes in the measurement chamber.

23. The osmolarity measuring system of claim 18, wherein the base unit further comprises a network interface.

24. The osmolarity measuring system of claim 23, wherein the processor is configured to download the plurality of osmolarity measurements through the network interface.

25. A test kit comprising:
a set of contact lenses; and
an osmolarity measuring system, the osmolarity system comprising:
  a measurement chamber configured to receive a volume of fluid and to receive a contact lens, the contact lens configured to carry a certain amount of tear film,
  a series of electrodes configured to measure the electrical properties of fluid in the measurement chamber, and
  a processing device coupled to the series of electrodes, the processing device configured to detect a change in the electrical properties of the fluid in the measurement chamber when a lens is placed in the measurement chamber.

26. The test kit of claim 25, wherein the processing device is configured to correlate the change in electrical properties with an osmolarity measurement.

27. The test kit of claim 26, wherein the osmolarity measurement system further comprises a plurality of electrode pairs, the plurality of electrode pairs configured to measure the electrical properties of the fluid.

28. The test kit of claim 27, wherein the pair of electrodes is configured to avoid direct contact with the contact lens when the contact lens is placed in the measuring chamber.

29. The test kit of claim 25, wherein detecting a change in the electrical properties comprises measuring the electrical conductivity of the fluid.

30. The test kit of claim 25, wherein the fluid is deionized water.

31. The test kit of claim 26, wherein the osmolarity measuring system further comprises a display coupled with the processing device, wherein the processing device is further configured to display the osmolarity measurement on the display.

32. The test kit of claim 26, wherein the osmolarity measurement system further comprises a memory coupled with the processing device, the memory configured to store a table that maps electrical properties with osmolarity values, and wherein the processor is configured to correlate the change in electrical properties with an osmolarity value using the table.

33. The test kit of claim 32, wherein the table is configured to account for a baseline osmolarity associated with the volume of fluid that the measurement chamber is configured to receive.

34. The test kit of claim 33, wherein the memory is configured to store a plurality of osmolarity measurements.

35. The test kit of claim 34, wherein the memory is removable.

36. The test kit of claim 34, wherein the processor is further configured to track trends in the plurality of osmolarity measurements.

37. The test kit of claim 36, wherein the osmolarity measuring system further comprises an indicator to tell the user to select a new contact lens from the set of contact lenses.

38. The test kit of claim 37, wherein the indicator comprises at least one of a display, an LED, a plurality of lights, or an auditory signal.

39. The test kit of claim 38, wherein the set of contact lenses further comprises an array of coded packages, and wherein each of the packages in the array of coded packages is configured to include contact lenses with different properties than those associated with the contact lenses in the other packages in the array.

40. The test kit of claim 39, wherein the contact lens properties include porosity, composition, and stiffness, contact lens design parameters that can be modulated to varying tear film osmolarities.

41. The test kit of claim 39, wherein the indicator can be configured to indicate which package of the array of coded packages should be used.

42. A test kit comprising:
a set of artificial tear solutions an osmolarity measuring system; and
an osmolarity measuring system, the osmolarity system comprising:
  a measurement chamber configured to receive a volume of fluid and to receive a contact lens, the contact lens configured to carry a certain amount of tear film,
  a series of electrodes configured to measure the electrical properties of fluid in the measurement chamber, and
  a processing device coupled to the series of electrodes, the processing device configured to detect a change in the electrical properties of the fluid in the measurement chamber when a lens is placed in the measurement chamber.

43. The test kit of claim 42, wherein the processing device is configured to correlate the change in electrical properties with an osmolarity measurement.

44. The test kit of claim 43, wherein the osmolarity measurement system further comprises a plurality of electrode pairs, the plurality of electrode pairs configured to measure the electrical properties of the fluid.

45. The test kit of claim 44, wherein the pair of electrodes is configured to avoid direct contact with the contact lens when the contact lens is planed in the measuring chamber.

46. The test kit of claim 42, wherein detecting a change in the electrical properties comprises measuring the electrical conductivity of the fluid.

47. The test kit of claim 42, wherein the fluid is deionized water.

48. The test kit of claim 43, wherein the osmolarity measuring system further comprises a display coupled with the processing device, wherein the processing device is further configured to display the osmolarity measurement on the display.

49. The test kit of claim 43, wherein the osmolarity measurement system further comprises a memory coupled with the processing device, the memory configured to store a table that maps electrical properties with osmolarity values, and wherein the processor is configured to correlate the change in electrical properties with an osmolarity value using the table.

50. The test kit of claim 49, wherein the table is configured to account for a baseline osmolarity associated with the volume of fluid that the measurement chamber is configured to receive.

51. The test kit of claim 50, wherein the memory is configured to store a plurality of osmolarity measurements.

52. The test kit of claim 51, wherein the memory is removable.

53. The test kit of claim 51, wherein the processor is further configured to track trends in the plurality of osmolarity measurements.

54. The test kit of claim 53, wherein the osmolarity measuring system further comprises an indicator to tell the user to select a new artificial tear solution from the set of artificial tear solutions.

55. The test kit of claim 54, wherein the indicator comprises at least one of a display, an LED, a plurality of lights, or an auditory signal.

56. The test kit of claim 55, wherein the set of artificial tear solutions further comprises an array of coded packages, and wherein each of the packages in the array of coded packages is configured to include artificial tear solutions with different properties than those associated with the artificial tear solutions in the other packages in the array.

57. The test kit of claim 56, wherein the artificial tear solutions properties include: isotonic, hypotonic, and hypertonic properties, formulation characteristics that can be designed to address varying tear film osmolarities.

58. The test kit of claim 56, wherein the indicator can be configured to indicate which package of the array of coded packages should be used.

59. A test kit comprising:
a set of medications;
an osmolarity measuring system, the osmolarity system comprising:
a measurement chamber configured to receive a volume of fluid and to receive a contact lens, the contact lens configured to carry a certain amount of tear film,
a series of electrodes configured to measure the electrical properties of fluid in the measurement chamber, and
a processing device coupled to the series of electrodes, the processing device configured to detect a change in the electrical properties of the fluid in the measurement chamber when a lens is placed in the measurement chamber.

60. The test kit of claim 59, wherein the processing device is configured to correlate the change in electrical properties with an osmolarity measurement.

61. The test kit of claim 60, wherein the osmolarity measurement system further comprises a plurality of electrode pairs, the plurality of electrode pairs configured to measure the electrical properties of the fluid.

62. The test kit of claim 61, wherein the pair of electrodes is configured to avoid direct contact with the contact lens when the contact lens is placed in the measuring chamber.

63. The test kit of claim 59, wherein detecting a change in the electrical properties comprises measuring the electrical conductivity of the fluid.

64. The test kit of claim 60, wherein the fluid is deionized water.

65. The test kit of claim 60, wherein the osmolarity measuring system further comprises a display coupled with the processing device, wherein the processing device is further configured to display the osmolarity measurement on the display.

66. The test kit of claim 60, wherein the osmolarity measurement system further comprises a memory coupled with the processing device, the memory configured to store a table that maps electrical properties with osmolarity values, and wherein the processor is configured to correlate the change in electrical properties with an osmolarity value using the table.

67. The test kit of claim 66, wherein the table is configured to account for a baseline osmolarity associated with the volume of fluid that the measurement chamber is configured to receive.

68. The test kit of claim 67, wherein the memory is configured to store a plurality of osmolarity measurements.

69. The test kit of claim 68, wherein the memory is removable.

70. The test kit of claim 68, wherein the processor is further configured to track trends in the plurality of osmolarity measurements.

71. The test kit of claim 70, wherein the osmolarity measuring system further comprises an indicator to tell the user to select a new medication from the set of medications.

72. The test kit of claim 71, wherein the indicator comprises at least one of a display, an LED, a plurality of lights, or an auditory signal.

73. The test kit of claim 72, wherein the set of medications further comprises an array of coded packages, and wherein each of the packages in the array of coded packages is configured to include medications with different properties than those associated with the medications in the other packages in the array.

74. The test kit of claim 73, wherein the artificial tear solutions properties include isotonic, hypotonic, and hypertonic properties.

75. A method for configuring an osmolarity testing device comprising the steps of:
determining a volume of a fluid to be used when testing osmolarity using the osmolarity testing device;
measuring electrical properties associated with the determined fluid volume;
establishing a baseline osmolarity value for the osmolarity testing device based on the measured electrical properties associated with the determined fluid volume; and
providing a table that maps measured electrical properties to osmolarity values.

76. The method of claim 75, wherein the table is configured to account for the established baseline osmolarity value.

* * * * *